United States Patent

Breuer et al.

[11] 4,038,271
[45] July 26, 1977

[54] [[[(2,4-DIOXO-1-IMIDAZOLIDINYL-)AMINO]-CARBONYL]AMINO]ACETYL-PENICILLIN DERIVATIVES

[75] Inventors: Hermann Breuer; Uwe D. Treuner, both of Regensburg, Germany

[73] Assignee: E. R. Squibb & Sons, Inc., Princeton, N.J.

[21] Appl. No.: 740,163

[22] Filed: Nov. 8, 1976

[51] Int. Cl.² .................. C07D 499/64; C07D 499/66; C07D 499/68; C07D 499/70
[52] U.S. Cl. .................................. 260/239.1; 424/271
[58] Field of Search ..................................... 260/239.1

[56] References Cited

U.S. PATENT DOCUMENTS

| | | | |
|---|---|---|---|
| 3,340,252 | 9/1967 | Alburn et al. | 260/239.1 |
| 3,720,665 | 3/1973 | Welch et al. | 260/239.1 |
| 3,870,709 | 3/1975 | Hamanaka | 260/239.1 |
| 3,935,192 | 1/1976 | Ferres et al. | 260/239.1 |

*Primary Examiner*—Gerald A. Schwartz
*Attorney, Agent, or Firm*—Lawrence S. Levinson; Merle J. Smith; Stephen B. Davis

[57] ABSTRACT

[[[(2,4-Dioxo-1-imidazolidinyl)amino]carbonyl]amino]-acetylpenicillin derivatives of the formula

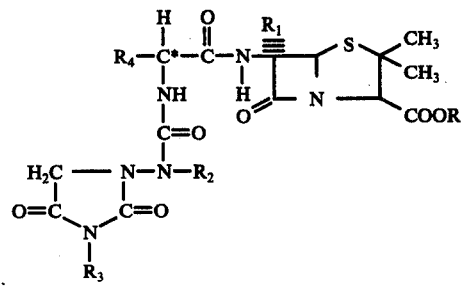

wherein R is hydrogen, lower alkyl, phenyl-lower alkyl, tri(lower alkyl)silyl, a salt forming ion, or the group

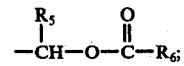

$R_1$ is hydrogen or methoxy; $R_2$, $R_3$ and $R_5$ each are independently selected from hydrogen and lower alkyl; $R_4$ is hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups; $R_6$ is lower alkyl; are disclosed. These compounds are useful as antibacterial agents.

32 Claims, No Drawings

[[[(2,4-DIOXO-1-IMIDAZOLIDINYL)AMINO]-CARBONYL]AMINO]ACETYLPENICILLIN DERIVATIVES

BACKGROUND OF THE INVENTION

Various ureido substituted acetamidopenicillins are disclosed as possessing useful antibacterial activity by Fosker in U.S. Pat. No. 3,352,851, Erickson in U.S. Pat. No. 3,720,664, and Welch et al. in U.S. Pat. No. 3,720,665. Also disclosed as possessing useful antibacterial activity are various substituted ureido containing penicillins such as those disclosed by Ferres et al. in U.S. Pat. Nos. 3,923,788; 3,926,960; 3,935,189; 3,935,192; 3,957,759; and 3,962,216; by Disselnkotter et al. in U.S. Pat. Nos. 3,933,795; 3,936,442; 3,939,149; and 3,959,258; by Schrock et al. in U.S. Pat. No. 3,923,789 and by Murakami et al. in U.S. Pat. No. 3,939,150.

SUMMARY OF THE INVENTION

This invention relates to new [[[(2,4-dioxo-1-imidazolidinyl)amino]carbonyl]amino]acetylpenicillin derivatives of the formula $$ (I) $$

R represents hydrogen, lower alkyl, phenyl-lower alkyl, tri(lower alkyl) silyl, a salt forming ion, or the group $$-CH-O-\overset{O}{\underset{\|}{C}}-R_6$$
$$\underset{R_5}{|}$$

wherein $R_5$ is hydrogen or lower alkyl and $R_6$ is lower alkyl.

$R_1$ represents hydrogen or methoxy. The $R_1$ substituent is in the α-configuration as indicated by the broken lines (≡).

$R_2$ and $R_3$ each represents hydrogen or lower alkyl.

$R_4$ represents hydrogen, lower alkyl, cycloalkyl, cycloalkenyl, cycloalkadienyl, phenyl, phenyl-lower alkyl, substituted phenyl, substituted phenyl-lower alkyl, or certain heterocyclic groups.

DETAILED DESCRIPTION OF THE INVENTION

The various groups represented by the symbols have the meaning defined below and these definitions are retained throughout this specification.

The lower alkyl groups referred to throughout this specification include straight or branched chain hydrocarbon groups containing 1 to 8 carbon atoms, preferably 1 to 4 carbons. Examples of the type of groups contemplated are methyl, ethyl, propyl, isopropyl, butyl, t-butyl, etc. The lower alkoxy groups include such lower alkyl groups attached to an oxygen, e.g., methoxy, ethoxy, propoxy, etc. The phenyl-lower alkyl groups include such lower alkyl groups attached to a phenyl, preferably benzyl and phenethyl.

Cycloalkyl refers to groups having 3 to 7 carbons in the ring, i.e. cyclopropyl, cyclobutyl, cyclopentyl, cyclohexyl, and cycloheptyl. The term cycloalkenyl also represent rings having 3 to 7 carbons with one double bond, i.e. cyclobutenyl, cyclopentenyl, cyclohexenyl, etc. The term cycloalkadienyl represents a ring having 6 or 7 carbons with two double bonds located at various positions such as 1,4-cyclohexadienyl which is preferred.

The substituted phenyl and substituted phenyl-lower alkyl groups include one or two substituents selected from halogen (preferably chlorine or bromine), lower alkyl of 1 to 4 carbons (preferably methyl or ethyl), lower alkoxy of 1 to 4 carbons (preferably methoxy or ethoxy), and hydroxy, e.g. 2-, 3-, or 4-chlorophenyl, 2-, 3-, or 4-bromobenzyl, 2-, 3-, or 4-hydroxyphenyl, 3,5-dichlorophenyl, 2-, 3-, or 4-methylphenyl, 2-, 3-, or 4-ethoxyphenyl, etc.

The salt forming ions represented by R may be metal ions, e.g., aluminum, alkali metal ions such as sodium or potassium, alkaline earth metal ions such as calcium or magnesium, or an amine salt ion, of which a number are known for this purpose, for example, phenyl-lower alkylamines such as dibenzylamine, N,N-dibenzylethylenediamine, lower alkylamines such as methylamine, triethylamine, and N-lower alkylpiperidines such as N-ethylpiperidine. Sodium and potassium are the preferred salt forming ions.

The halogens are the four common halogens, of which chlorine and bromine are preferred.

Trimethylsilyl is the preferred tri(lower alkyl) silyl group.

The heterocyclic groups represented by $R_4$ are 2-thienyl, 3-thienyl, 2-furyl, 3-furyl, 2-pyridyl, 3-pyridyl, or 4-pyridyl. Also included within the meaning of $R_4$ are such heterocyclics having a halogen (preferably chlorine or bromine) or a lower alkyl of 1 to 4 carbons (preferably methyl or ethyl) substituent, i.e. 2-(4-chlorothienyl), 3-(4-methylthienyl), etc.

The new compounds of formula I can be prepared by several methods. For example an α-amino intermediate of the formula $$ (II) $$

can be reacted with a 2,4-dioxo-1-imidazolidine compound of the formula $$ (III) $$

or $$ (IV) $$

-continued

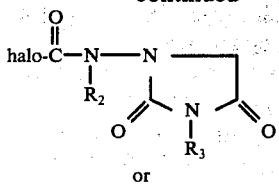
(V)

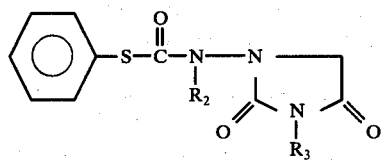

wherein $R_2$ and $R_3$ are as defined above and halo is chlorine or bromine. Preferably this reaction is between the acid chloride compound of formula IV and the trialkylsilyl derivative of the α-amino compound of formula II and as the last step of the reaction the product is hydrolyzed with water to remove the trialkylsilyl protecting group and yield the compound of formula I wherein R is hydrogen. When the reaction is between the α-amino compound of formula II and the intermediate of formula III or V, it is preferably performed in the presence of a base such as triethylamine.

The preparation of the α-amino compounds of formula II wherein $R_1$ is hydrogen are disclosed in various references including U.S. Pat. Nos. 2,985,648, 3,342,677, 3,485,819, etc., and the α-amino compounds wherein $R_1$ is methoxy are disclosed in various references including British Patent 1,339,007, U.S. Pat. No. 3,954,731, etc.

The compounds of formula I can also be prepared by acylating a 6-amino compound of the formula

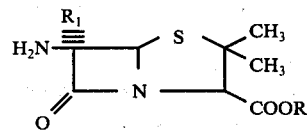
(VI)

preferably wherein R is trimethylsilyl or benzyl, with a compound of the formula

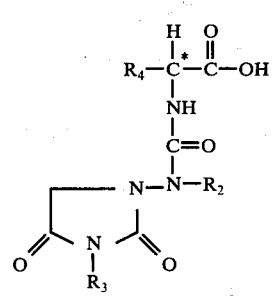
(VII)

or a derivative thereof wherein the hydroxy group is replaced with a known activating group such as an acid chloride, mixed anhydride or an activated ester such as

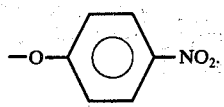

The reaction can optionally be performed in the presence of dicyclohexylcarbodiimide. The resulting product is then treated according to methods known in the art to remove the ester protecting group and yield the compound of formula I wherein R is hydrogen.

The compound of formula VII is prepared by reacting the isocyanate acid ester of the formula

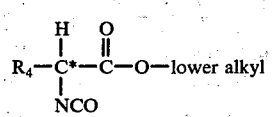
(VIII)

with the 1-amino-2,4-dioxoimidazolidine of the formula

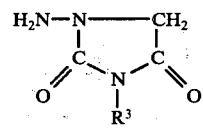
(IX)

or by reacting an α-amino acid of the formula

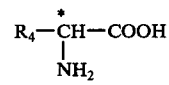
(X)

preferably as the trimethylsilyl ester, with the acyl halide of formula IV, in an organic medium such as acetonitrile.

The starting materials of formula VIII are produced from the corresponding α-amino acid by reaction with phosgene in toluene by the method of Goldschmidt et al., Annalen der Chemie 575, 217 (1951). The 1-amino-2,4-dioxoimidazolidines of formula IX are produced according to the method described in Monatsch 85, 607 (1954).

The compounds of formula I wherein R is lower alkyl, phenyl-lower alkyl, or the acyloxymethyl group

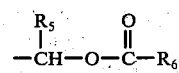

are obtained by reacting the 6-aminopenicillin of formula VI either before or after the acylation of the 6-aminosubstituent with one or two moles of a compound of the formula halo-R  (XI)

or $R=N^+=N^-$  (XII)

wherein halo is preferably chlorine or bromine in an inert solvent such as dimethylformamide, acetone, dioxane, benzene, or the like at about ambient temperature or below.

Similarly, the compounds of formula I wherein R is tri(lower alkyl)silyl are obtained by introducing such groups onto the penicillanic acid moiety either before or after the acylation reaction.

The carboxylate salts of the compound of formula I are formed by reacting the carboxyl group of the penicillanic acid moiety, i.e., R is hydrogen, with any of the salt forming ions described above.

Additional experimental details are found in the examples.

It will be appreciated that the compounds of formula I are optically active due to the presence of an asymmetric carbon atom represented as C* in the preceding formulas. By selection of the appropriate starting material it is possible to obtain the compounds of formula I as a mixture of optically active isomers or isolated as a single isomer. The various isomers as well as their mixtures are within the scope of this invention.

Preferred compounds of this invention are the acids and metal salts of formula I wherein $R_4$ is cyclohexenyl, cyclohexadienyl, phenyl, benzyl, phenethyl, substituted phenyl, benzyl or phenethyl wherein the substituent is on the phenyl ring and is one or two members selected from chloro, bromo, methyl, ethyl, methoxy, ethoxy and hydroxy or a substituted or unsubstituted heterocyclic selected from 2-thienyl, 3-thienyl, 2-furyl, 3-furyl, 2-pyridyl, 3-pyridyl and 4-pyridyl wherein the heterocyclic substituent is chloro, bromo, methyl or ethyl; and $R_2$ and $R_3$ are hydrogen, methyl, or ethyl.

The most preferred final compounds are the acids and alkali metal salts such as sodium or potassium of formula I wherein $R_4$ is 2-thienyl, 3-thienyl, phenyl or 4-hydroxyphenyl; and $R_2$ is hydrogen and $R_3$ is hydrogen or methyl.

The compounds of formula I have a broad spectrum of antibacterial activity against both gram positive and gram negative organisms such as *Staphylococcus aureus, Salmonella schottmuelleri, Pseudomonas aeruginosa, Proteus rettgeri, Escherichia coli, Enterobacter cloacae, Serratia marcescens*, etc. They may be used as antibacterial agents in a prophylactic manner or therapeutically to combat infections due to organisms such as those named above, and in general may be utilized in a manner similar to other penicillins. For example, a compound of formula I or a physiologically acceptable salt thereof may be used in various mammalian species such as mice, rats, dogs, etc., in an amount of about 1 to 100 mg./kg., daily, parenterally, in single or two to four divided doses to treat infections of bacterial origin, e.g., 5.0 mg./kg. in mice.

About 10 to 400 mg. of an acid compound of formula I or a physiologically acceptable salt thereof can be incorporated in an injectable form in a sterile aqueous vehicle such as water or a natural vegetable oil such as sesame oil, cottonseed oil, peanut oil, soybean oil or the like or a synthetic fatty vehicle such as ethyl oleate. Antioxidants, buffers, preservatives and the like may also be included. The material can also be prepared in dry form for reconstitution prior to administration with such vehicles.

The following examples are illustrative of the invention and constitute especially preferred embodiments. They also serve as models for the preparation of other members of the group which can be produced by suitable substitution of starting materials. All temperatures are in degrees celsius.

EXAMPLE 1

6β-[[D-[[[(2,4-Dioxo-1-imidazolidinyl)amino]carbonyl]amino]-phenylacetyl]amino]-3,3-dimethyl-7-oxo-4-thia-1-azabicyclo-[3.2.0]heptane-2-carboxylic acid, sodium salt a. 1-[(Chlorocarbonyl)amino]-2,4-imidazolidinedione 11.5 g. (0.1 mole) of 1-amino-2,4-imidazolidinedione are thoroughly stirred into 150 ml. of absolute tetrahydrofuran. A solution of 15 g. (0.15 mole) of phosgene in 25 ml. of absolute tetrahydrofuran is added dropwise at 0°–5° over 20 minutes. The mixture is then stirred for 3 hours at room temperature. An almost clear solution results. This is filtered and the solvent is evaporated in vacuum. The oily residue crystallizes on trituration with petroleum ether to yield 17.2 g. of 1-[(chlorocarbonyl)amino]-2,4-imidazolidinedione; m.p. 126° (dec.).

b. 6β-[[D-[[[(2,4-Dioxo-1-imidazolidinyl)amino]carbonyl]amino]-phenylacetyl]amino]-3,3-dimethyl-7-oxo-4-thia-1-azabicyclo-[3.2.0]heptane-2-carboxylic acid 3.17 g. (0.01 mole) of anhydrous 6β-[D-(2-amino-2-phenylacetamido)]-3,3-dimethyl-7-oxo-4-thia-1-azabicyclo-[3.2.0]heptane-2-carboxylic acid (i.e. ampicillin) are suspended in 80 ml. of anhydrous acetonitrile and brought into solution by the addition of 10 ml. of bistrimethylsilylacetamide. 20 ml. of propylene oxide are added, the mixture is cooled to 0° and a solution of 1.95 g. (0.011 mole) of 1-[(chlorocarbonyl)amino]-2,4-imidazolidinedione, from part (a), in acetonitrile is added dropwise with stirring. The reaction mixture is stirred for an additional ½ hour at 0° and 1½ hours at room temperature. Afterward, 10 ml. of water are added at about 10°, the mixture is stirred for 5 minutes and 150 ml. of ethyl acetate are added. After stirring vigorously, the phases are separated, the aqueous phase is extracted once more with ethyl acetate and the combined extracts are washed twice with a small amount of water. After drying, the product is triturated with ether and filtered under suction to yield 3.7 g. of 6β-[[D-[[[(2,4-dioxo-1-imidazolidinyl)amino]carbonyl]-amino]-phenylacetyl]amino]-3,3-dimethyl-7-oxo-4-thia-1-azabicyclo[3.2.0]heptane-2-carboxylic acid; m.p. 176°–178° (dec.).

c. 6β-[[D-[[[(2,4-Dioxo-1-imidazolidinyl)amino]carbonyl]amino]-phenylacetyl]amino]-3,3-dimethyl-7-oxo-4-thia-1-azabicyclo[3.2.0]heptane-2-carboxylic acid, sodium salt The acid product from part (b) is brought into solution with 12 ml. of methanol and the solution is treated with an equivalent proportion of aqueous sodium ethyl hexanoate solution. 12 ml. of ether are added slowly to the clear solution which is then stirred for 10 minutes. The precipitate is filtered off to yield 2.9 g. of 6β-[[D-[[[(2,4-dioxo-1-imidazolidinyl)amino]carbonyl]amino]-phenylacetyl]amino]-3,3-dimethyl-7-oxo-4-thia-1-azabicyclo[3.2.0]heptane-2-carboxylic acid, sodium salt; m.p. 209°–210° (dec.).

Similarly, by substituting aqueous potassium ethyl hexanoate for the sodium ethyl hexanoate in the above procedure one obtains 6β-[[D-[[[(2,4-dioxo-1-imidazolidinyl)-amino]carbonyl]amino]phenylacetyl]amino]-3,3-dimethyl-7-oxo-4-thia-1-azabicyclo[3.2.0]-heptane-2-carboxylic acid, potassium salt.

EXAMPLES 2–3

Similarly, by substituting an equivalent amount of 6β-[L-(2-amino-2-phenylacetamido)]-3,3-dimethyl-7- oxo-4-thia-1-azabicyclo[3.2.0]heptane-2-carboxylic acid, and 6β-[D,L-(2-amino-2-phenylacetamido)]-3,3-dimethyl-7-oxo-4-thia-1-azabicyclo[3.2.0]heptane-2-carboxylic acid, for the ampicillin in example 1, one obtains:

6β-[[L-[[[(2,4-dioxo-1-imidazolidinyl)amino]carbonyl]-amino]phenylacetyl]amino]-3,3-dimethyl-7-oxo-4-thia-1-azabicyclo[3.2.0]heptane-2-carboxylic acid, and 6β-[[D,L-[[[(2,4-dioxo-1-imidazolidinyl)amino]carbonyl]-amino]phenylacetyl]amino]-3,3-dimethyl-7-oxo-4-thia-1-azabicyclo-[3.2.0]heptane-2-carboxylic acid, respectively.

These acid compounds can then be converted to the sodium or potassium salt as taught in example 1(c).

EXAMPLE 4

6β-[[D-[[[(3-Methyl-2,4-dioxo-1-imidazolidinyl)amino]carbonyl]-amino]phenylacetyl]amino]-3,3-dimethyl-7-oxo-4-thia-1-azabicyclo[3.2.0]heptane-2-carboxylic acid, sodium salt a. 3-Methyl-1-[(phenylmethylene)amino]-2,4-imidazolidinedione 60.9 g. (0.3 mole) of 1-[(phenylmethylene)amino]-2,4-imidazolidinedione are suspended in 450 ml. of absolute methanol and 150 ml. (0.3 mole) of 2N sodium methylate solution are added to the suspension. A clear solution results and 63.9 g. (0.45 mole) of methyl iodide are added dropwise over a period of ten minutes. After a short period of time, crystals precipitate. The mixture is stirred overnight, filtered under suction, and washed with methanol to yield 50.9 g. of 3-methyl-1-[(phenylmethylene)amino]-2,4-imidazolidinedione; m.p. 253°–255°.

b. 1-Amino-3-methyl-2,4-imidazolidinedione

A mixture of 25.3 g. of 3-methyl-1-[(phenylmethylene)-amino]-2,4-imidazolidinedione from part (a), 200 ml. of concentrated hydrochloric acid and 200 ml. of water are distilled for 90 minutes. The mixture is cooled, filtered and the filtrate is evaporated to dryness to yield 9.2 g. of 1-amino-3-methyl-2,4-imidazolidinedione, hydrochloride; m.p. 162°–165°.

9.1 g. of this hydrochloride salt together with 160 ml. of methanol and 27.5 ml. of 2N sodium methylate solution are refluxed for 15 minutes. After cooling, the reaction mixture is filtered and the filtrate is evaporated to dryness. The residue is recrystallized from a small amount of ethanol to yield 6.2 g. of 1-amino-3-methyl-2,4-imidazolidinedione; m.p. 113°–118°.

c. 1-[(Chlorocarbonyl)amino]-3-methyl-2,4-imidazolidinedione 1.29 g. (0.01 mole) of 1-amino-3-methyl-2,4-imidazolidinedione from part (b) are suspended in 20 ml. of absolute tetrahydrofuran. The suspension is cooled to 0° and a solution of 1.5 g. (0.015 mole) of phosgene in 3.5 g. of tetrahydrofuran is added. After 20 minutes, a clear solution results. After two hours, the solution is evaporated to dryness, the residue is triturated with petroleum ether and filtered under suction to yield 1.8 g. of 1-[(chlorocarbonyl)-amino]-3-methyl-2,4-imidazolidinedione.

d. 6β-[[D-[[[(3-Methyl-2,4-dioxo-1-imidazolidinyl)amino]carbonyl]-amino]phenylacetyl]amino]-3,3-dimethyl-7-oxo-4-thia-1-azabicyclo[3.2.0]heptane-2-carboxylic acid 0.0055 Moles of 1-[(chlorocarbonyl)amino]-3-methyl-2,4-imidazolidinedione from part (c) and 1.74 g. (0.005 mole) of ampicillin are reacted according to the procedure of example 1(b) to yield 2.2 g. of 6β-[[D-[[[(3-methyl-2,4-dioxo-1-imidazolidinyl)amino]carbonyl]-amino]phenylacetyl]-amino]-3,3-dimethyl-7-oxo-4-thia-1-azabicyclo[3.2.0]heptane-2-carboxylic acid.

e. 6β-[-azabicycloD-[3.2.0](3-Methyl-2,4-dioxo-1-imidazolidinyl)amino]-carbonyl]amino]phenylacetyl]amino]-3,3-dimethyl-7-oxo-4-thia-1-azabicyclo[3.2.0]-heptane-2-carboxylic acid, sodium salt The acid product from part (d) is dissolved in 5 ml. of methanol. 4.2 ml. of 1N sodium ethylhexanoate solution are added and the mixture is poured into 200 ml. of ether. The precipitate is filtered off to yield 2.0 g. of 6β-[[D-[[[(3-methyl-2,4-dioxo-1-imidazolidinyl)amino]-carbonyl]amino]phenylacetyl]amino]-3,3-dimethyl-7-oxo-4-thia-1-azabicyclo[3.2.0]heptane-2-carboxylic acid, sodium salt; m.p. 199°–204° (dec.).

Substituting aqueous potassium ethyl hexanoate for the sodium ethyl hexanoate in the above procedure one obtains the corresponding potassium salt.

Also, substituting the L- and D,L- isomeric starting materials from examples 2 and 3 for the ampicillin in part (d) one obtains:

6β-[[L-[[[(3-methyl-2,4-dioxo-1-imidazolidinyl)amino]-carbonyl]amino]phenylacetyl]amino]-3,3-dimethyl-7-oxo-4-thia-1-azabicyclo[3.2.0]heptane-2-carboxylic acid, and 6β-[[D,L-[[[(3-methyl-2,4-dioxo-1-imidazolidinyl)amino]-carbonyl]amino]phenylacetyl]amino]-3,3-dimethyl-7-oxo-4-thia-1-azabicyclo[3.2.0]heptane-2-carboxylic acid; respectively.

EXAMPLES 5–36

Following the procedure of example 1 but employing the 2,4-dioxoimidazolidine shown in Col. I and the 6β-acyl-6β-methoxy or desmethoxy penicillanic acid shown in Col. II one obtains the product shown in Col. III. The penicillanic acid reactant shown in Col. II and the final product shown in Col. III can be in the D-, L- or D,L-form.

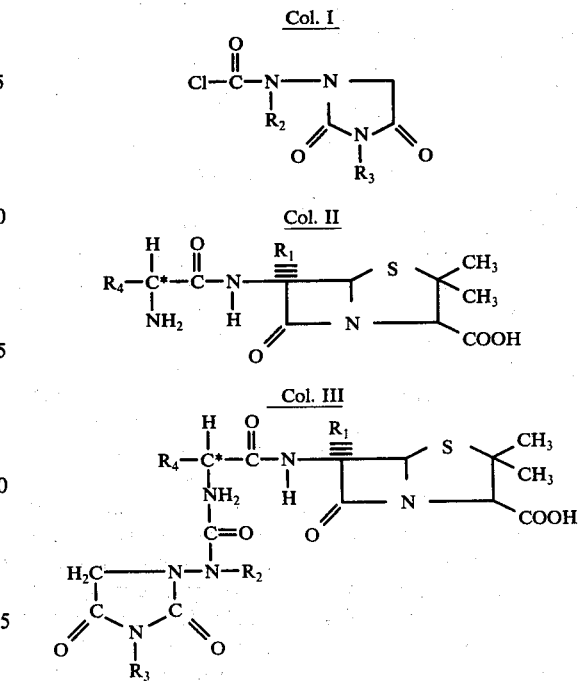

| Ex. | R₁ | R₄ | R₂ | R₃ |
|---|---|---|---|---|
| 5 | —OCH₃ |  | —H | —H |
| 6 | —OCH₃ |  | —CH₃ | —H |
| 7 | —H | 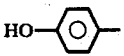 | —H | —H |
| 8 | —OCH₃ | 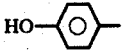 | —H | —CH₃ |
| 9 | —H | 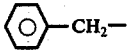 | —H | —H |
| 10 | —OCH₃ | 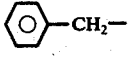 | —C₂H₅ | —H |
| 11 | —H | 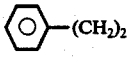 | —H | —CH₃ |
| 12 | —H | 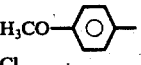 | —H | —C₂H₅ |
| 13 | —OCH₃ | 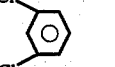 | —CH₃ | —CH₃ |
| 14 | —H |  | —CH₃ | —C₂H₅ |
| 15 | —H | 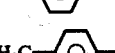 | —H | n-C₃H₇ |
| 16 | —OCH₃ | 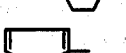 | —H | —H |
| 17 | —H | 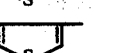 | —H | —H |
| 18 | —H | 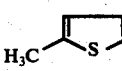 | —H | —CH₃ |
| 19 | —OCH₃ |  | —CH₃ | —H |
| 20 | —H | 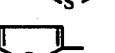 | —CH₃ | —CH₃ |
| 21 | —OCH₃ | 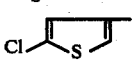 | t-C₄H₉ | —H |
| 22 | —H | 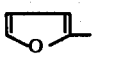 | —H | —H |
| 23 | —OCH₃ | 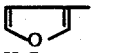 | —H | —H |
| 24 | —H | 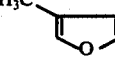 | —H | —CH₃ |
| 25 | —OCH₃ | 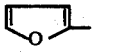 | —C₂H₅ | —C₂H₅ |
| 26 | —H | 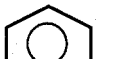 | —H | —H |
| 27 | —OCH₃ | 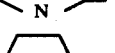 | —H | —H |
| 28 | —H |  | —H | —CH₃ |
| 29 | —OCH₃ |  | —H | —H |
| 30 | —H |  | —H | —H |
| 31 | —H |  | —CH₃ | —CH₃ |
| 32 | —H |  | —H | —CH₃ |
| 33 | —OCH₃ |  | —H | —H |
| 34 | —H |  | —H | —CH₃ |
| 35 | —H | —H | —H | —H |
| 36 | —H | C₂H₅— | —H | —H |

The final compounds of examples 5 to 36 can be converted to the various salts or esters disclosed in the preceding specification by methods known in the art.

EXAMPLE 37

6β-[[D-[[[(2,4-Dioxo-1-imidazolidinyl)amino]carbonyl]amino]-2-thienylacetyl]amino]-3,3-dimethyl-7-oxo-4-thia-1-azabicyclo[3.2.0]heptane-2-carboxylic acid a. D-α-[[[(2,4-Dioxo-1-imidazolidinyl)amino]carbonyl]amino]-2-thiopheneacetic acid 11.5 g. (0.073 mole) of D-α-amino-2-thiopheneacetic acid are suspended in 220 ml. of acetonitrile and brought into solution by the addition of 55 ml. of bis-trimethylsilylacetamide. 55 ml. of propylene oxide are added and 15.5 g. (20% excess) of 1-(chlorocarbonylamino)-2,4-dioxoimidazolidine from example 1(a) are added at room temperature with stirring. The reaction proceeds for four hours. Afterwards, the reaction mixture is evaporated to dryness, water is added, the pH is adjusted to 7 and the mixture is again concentrated. The residue is triturated with ether and filtered under suction. The product (approximately 37 g.) is treated with 43 ml. of 2N hydrochloric acid. From the initially clear solution crystals precipitate after a short time and the crystals are filtered under suction. Recrystallization from water yields 11.7 g. of D-α-[[[(2,4-dioxo-1-imidazolidinyl)amino]carbonyl]amino]-2-thiopheneacetic acid; m.p. 200°–203° (dec.).

b. 6β-[[D-[[[(2,4-Dioxo-1-imidazolidinyl)amino]carbonyl]amino]-2-thienylacetyl]amino]-3,3-dimethyl-7-oxo-4-thia-1-azabicyclo[3.2.0]heptane-2-carboxylic acid 2.16 g. (0.01 mole) of 6β-amino penicillanic acid are suspended in 30 ml. of anhydrous acetonitrile and 6.8 ml. of bistrimethylsilylacetamide are added. The 6β-amino penicillanic acid goes into solution as the trimethylsilyl ester over the course of an hour.

A mixed anhydride is formed from 2.98 g. (0.01 mole) of D-α-[[[2,4-dioxo-1-imidazolidinyl)amino]carbonyl]amino]-2-thiopheneacetic acid from part (a), 1.35 g. (0.01 mole) of N,N-dimethylbenzylamine and 1.03 g. (0.01 mole) of methylchloroformate in acetonitrile at −20°. The solution of 6β-amino penicillanic acid trimethylsilyl ester is added dropwise at −20° over a period of 10 minutes to the solution of the mixed anhydride. The resulting mixture is stirred for 2½ hours at −10°. The temperature is then allowed to rise to room temperature, the mixture is treated with 200 ml. of ethyl acetate and 30 ml. of water, cooled to 0° C and adjusted to pH 2 with 2N hydrochloric acid. The ethyl acetate phase is concentrated and the residue treated with ether to yield 6β-[[D-[[[(2,4-dioxo-1-imidazolidinyl)amino]carbonyl]amino]-2-thienylacetyl]amino]-3,3-dimethyl- 7-oxo-4-thia-1-azabicyclo[3.2.0]heptane-2-carboxylic acid.

An aqueous equimolar solution of this acid and sodium bicarbonate is lyophilized to yield the sodium salt of this acid. Similarly, by employing potassium bicarbonate one can obtain the corresponding potassium salt.

Following the above procedure but substituting L-α-amino-2-thiopheneacetic acid for the D-form in part (a), one obtains 6β-[[L-[[[(2,4-dioxo-1-imidazolidinyl)amino]carbonyl]-amino]-2-thienylacetyl]amino]-3,3-dimethyl-7-oxo-4-thia-1-azabicyclo[3.2.0]heptane-2-carboxylic acid.

EXAMPLE 38

6β-[[D,L-[[[(2,4-Dioxo-1-imidazolidinyl)amino]carbonyl]amino]-phenylacetyl]amino]-3,3-dimethyl-7-oxo-4-thia-1-azabicyclo[3.2.0]heptane-2-carboxylic acid a. D,L-α-[[[(2,4-Dioxo-1-imidazolidinyl)amino]carbonyl]amino]-benzeneacetic acid, ethyl ester 1.15 g. (0.01 mol.) of 1-amino-2,4-dioxoimidazolidine are dissolved in 50 ml. of dioxane while heating. The solution is permitted to cool to room temperature while stirring, wherein a portion of the 1-amino-2,4-dioxoimidazolidine crystallizes out. 2.05 g. (0.01 mol.) of α-isocyanatobenzeneacetic acid, ethyl ester are added and the reation mixture is stirred overnight at room temperature. On the next day the mixture is concentrated and the residue is triturated with ether. 3.0 g. of α-[[[(2,4-dioxo-1-imidazolidinyl)amino]-carbonyl]amino]benzeneacetic acid, ethyl ester are obtained, m.p. 148°–151°.

b. D,L-α-[[[(2,4-Dioxo-1-imidazolidinyl)amino]carbonyl]amino]-benzene acetic acid 29.4 g. of D,L-α-[[[(2,4-dioxo-1-imidazolidinyl)amino]-carbonyl]amino]benzeneacetic acid, ethyl ester from part (a) are added to 138 ml. of 2N sodium hydroxide solution with stirring. The substance goes quickly into solution upon slight heating. The mixture is stirred for 2 hours at room temperature, filtered and the clean filtrate is acidified to pH 1 with concentrated hydrochloric acid. Upon rubbing, D,L-α-[[[(2,4-dioxo-1-imidazolidinyl)amino]carbonyl]amino]benzeneacetic acid crystallizes out. The mixture is let stand in the refrigerator overnight and then filtered under suction to yield 21.9 g., m.p. 139°–143°.

c. 6β-[[D,L-[[[(2,4-Dioxo-1-imidazolidinyl)amino]-carbonyl]amino]-phenylacetyl]amino]-7oxo-4-thia-1-azabicyclo[3.2.0]heptane-2-carboxylic acid The D,L-α-[[[(2,4-dioxo-1-imidazolidinyl)amino]carbonyl]-amino]benzene acetic acid from part (b) is converted to a mixed anhydride and reacted with 6β-amino penicillanic acid according to the procedure of example 37(b) to yield 6β-[[D,L-[[[(2,4-dioxo-1-imidazolidinyl)amino]carbonyl]amino]phenylacetyl]-amino]-7-oxo-4-thia-1-azabicyclo[3.2.0]heptane-2-carboxylic acid.

EXAMPLE 39

6β-[[D,L-[[[(2,4-Dioxo-1-imidazolidinyl)amino]carbonyl]amino]-2-thienylacetyl]amino]-3,3-dimethyl-7-oxo-4-thia-1-azabicyclo[3.2.0]heptane-2-carboxylic acid a. D,L-α-[[[(2,4-Dioxo-1-imidazolidinyl)amino]carbonyl]amino]-2-thiopheneacetic acid, ethyl ester By reacting 10.60 g. of D,L-α-isocyanato-2-thiopheneacetic acid, ethyl ester with 5.75 g. of 1-amino-2,4-dioxoimidazolidine in 250 ml. of dioxane according to the procedure of example 38, 15.6 g. of D,L-α-[[[(2,4-dioxo-1-imidazolidinyl)-amino]carbonyl]amino]-2-thiopheneacetic acid, ethyl ester are obtained, m.p. 151°–155°.

b. D,L-α-[[[(2,4-Dioxo-1-imidazolidinyl)amino]carbonyl]amino]-2-thiopheneacetic acid By mixing the D,L-α-[[[(2,4-dioxo-1-imidazolidinyl)-amino]carbonyl]amino]-2-thiopheneacetic acid, ethyl ester, from part (a), with sodium hydroxide solution and then acidifying according to the procedure of example 38(b), D,L-α-[[[(2,4-dioxo-1-imidazolidinyl)amino]carbonyl]amino]-2-thiopheneacetic acid is obtained, m.p. 193° (dec.).

c. 6β-[[D,L-[[[(2,4-Dioxo-1-imidazolidinyl)amino]-carbonyl]-amino]-2-thienylacetyl]amino]-3,3-dimethyl-7-oxo-4-thia-1-azabicyclo[3.2.0]heptane-2-carboxylic acid The D,L-α-[[[(2,4-dioxo-1-imidazolidinyl)amino]carbonyl]-amino]-2-thiopheneacetic acid from part (b) is converted to a mixed anhydride and reacted with 6β-amino penicillanic acid according to the procedure of example 37(b) to yield 6β-[[D,L-[[[(2,4-dioxoimidazolidinyl)amino]carbonyl]amino]-2-thienylacetyl]amino]-3,3-dimethyl-7-oxo-4-thia-1-azabicyclo[3.2.0]-heptane-2-carboxylic acid.

EXAMPLES 40–57

Following the procedure of example 37 but employing the substituted 2,4-dioxoimidazolidine shown in Col. I and the 6β-amino-6α-methoxy or desmethoxy penicillanic acid shown in Col. II one obtains the product shown in Col. III. The intermediate shown in Col. I and the final product shown in Col. III can be in the D-, L- or D,L-form.

Col. I

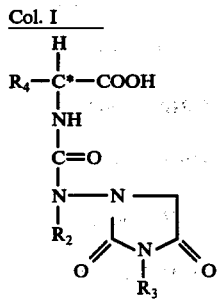

Col. II

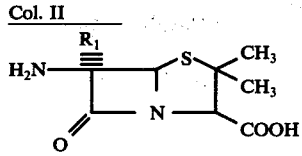

Col. III

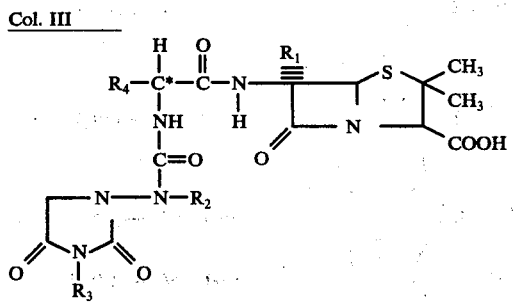

| Ex. | R₁ | R₄ | R₂ | R₃ |
|---|---|---|---|---|
| 40 | —OCH₃ | phenyl | —CH₃ | —CH₃ |
| 41 | —H | phenyl | —C₂H₅ | —C₂H₅ |
| 42 | —OCH₃ | 3-hydroxyphenyl | —H | —H |
| 43 | —H | 4-hydroxyphenyl | —H | —CH₃ |
| 44 | —OCH₃ | 4-hydroxyphenyl | —H | —H |
| 45 | —H | 4-chlorophenyl-(CH₂)₂— | —H | —H |
| 46 | —OCH₃ | phenyl-CH₂— | —H | —H |
| 47 | —H | 4-methylphenyl-CH₂— | —H | —CH₃ |
| 48 | —OCH₃ | 3-ethoxyphenyl-CH₂— | —CH₃ | —H |
| 49 | —OCH₃ | 2-thienyl | —H | —H |
| 50 | —H | 5-methyl-2-thienyl | —H | -i-C₃H₇ |
| 51 | —H | 2-furyl | —H | —CH₃ |
| 52 | —OCH₃ | 5-chloro-2-furyl | —H | —H |
| 53 | —H | 2-pyridyl | —CH₃ | —CH₃ |
| 54 | —OCH₃ | 2-pyridyl | —H | —CH₃ |
| 55 | —H | cyclohexyl | —H | —H |
| 56 | —OCH₃ | C₂H₅— | —H | —CH₃ |
| 57 | —H | 2-thienyl | —CH₃ | —C₂H₅ |

The final compounds of examples 40 to 57 can be converted to the various salts or esters disclosed in the preceding specification by methods known in the art.

What is claimed is:

1. A compound of the formula:

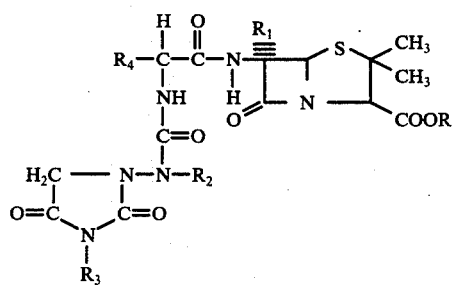

wherein R is hydrogen, lower alkyl, phenyl-lower alkyl, tri(lower alkyl)silyl, a conventional pharmaceutically acceptable salt forming ion, or $$-\underset{\underset{R_5}{|}}{CH}-O-\underset{\underset{O}{\|}}{C}-R_6;$$

$R_1$ is in the α-configuration and is hydrogen or methoxy; $R_2$, $R_3$ and $R_5$ each is hydrogen or lower alkyl; $R_4$ is hydrogen, lower alkyl, cycloalkyl of 3 to 7 carbons, cycloalkenyl of 3 to 7 carbons, cycloalkadienyl of 6 or 7 carbons, phenyl, phenyl-lower alkyl, substituted phenyl or phenyl-lower alkyl wherein said phenyl substituent is one or two members selected from the group consisting of halogen, lower alkyl, lower alkoxy and hydroxy, or a substituted or unsubstituted heterocyclic selected from the group consisting of 2-thienyl, 3-thienyl, 2-furyl, 3-furyl, 2-pyridyl, 3-pyridyl and 4-pyridyl wherein said heterocyclic substituent is attached at an available carbon atom and is halogen or lower alkyl; and $R_6$ is lower alkyl.

2. The compound of claim 1 wherein R is hydrogen or an alkali metal; $R_2$ and $R_3$ each is hydrogen, methyl, or ethyl; R$_4$ is cyclohexenyl, cyclohexadienyl, phenyl, benzyl, phenethyl, substituted phenyl, benzyl or phenethyl wherein said substituent is on the phenyl ring and is one or two members selected from the group consisting of chloro, bromo, methyl, ethyl, methoxy, ethoxy and hydroxy, or a substituted or unsubstituted heterocyclic selected from the group consisting of 2-thienyl, 3-thienyl, 2-furyl, 3-furyl, 2-pyridyl, 3-pyridyl, and 4-pyridyl wherein said heterocyclic substituent is attached at an available carbon atom and is chloro, bromo, methyl, or ethyl.

3. The compound of claim 2 wherein R$_1$ is hydrogen.

4. The compound of claim 3 wherein R is hydrogen, sodium, or potassium; R$_2$ is hydrogen; R$_3$ is hydrogen or methyl; and R$_4$ is 2-thienyl, 3-thienyl, phenyl or 4-hydroxyphenyl.

5. The compound of claim 4 wherein R$_3$ is hydrogen.

6. The compound of claim 5 wherein R$_4$ is 2-thienyl.

7. The compound of claim 6, 6β-[[D-[[[(2,4-dioxo-1-imidazolidinyl)amino]carbonyl]amino]-2-thienylacetyl]amino]-3,3-dimethyl-7-oxo-4-thia-1-azabicyclo[3.2.0]-heptane-2-carboxylic acid.

8. The sodium salt of the compound of claim 7.

9. The compound of claim 5 wherein R$_4$ is 3-thienyl.

10. The compound of claim 5 wherein R$_4$ is phenyl.

11. The compound of claim 10, 6β-[[D-[[[(2,4-dioxo-1-imidazolidinyl)amino]carbonyl]amino]phenylacetyl]amino]-3,3-dimethyl-7-oxo-4-thia-1-azabicyclo[3.2.0]-heptane-2-carboxylic acid.

12. The sodium salt of the compound of claim 11.

13. The compound of claim 5 wherein R$_4$ is 4-hydroxyphenyl.

14. The compound of claim 4 wherein R$_3$ is methyl.

15. The compound of claim 14 wherein R$_4$ is 2-thienyl.

16. The compound of claim 14 wherein R$_4$ is 3-thienyl.

17. The compound of claim 14 wherein R$_4$ is phenyl.

18. The compound of claim 17, 6β-[[D-[[[(3-methyl-2,4-dioxo-1-imidazolidinyl)amino]carbonyl]amino]-phenylacetyl]-amino]-3,3-dimethyl-7-oxo-4-thia-1-azabicyclo[3.2.0]heptane-2-carboxylic acid.

19. The sodium salt of the compound of claim 18.

20. The compound of claim 14 wherein R$_4$ is 4-hydroxyphenyl.

21. The compound of claim 2 wherein R$_1$ is methoxy.

22. The compound of claim 21 wherein R is hydrogen, sodium, or potassium; R$_2$ is hydrogen; R$_3$ is hydrogen or methyl; and R$_4$ is 2-thienyl, 3-thienyl, phenyl or 4-hydroxyphenyl.

23. The compound of claim 22 wherein R$_3$ is hydrogen.

24. The compound of claim 23 wherein R$_4$ is 2-thienyl.

25. The compound of claim 23 wherein R$_4$ is 3-thienyl.

26. The compound of claim 23 wherein R$_4$ is phenyl.

27. The compound of claim 23 wherein R$_4$ is 4-hydroxyphenyl.

28. The compound of claim 22 wherein R$_3$ is methyl.

29. The compound of claim 28 wherein R$_4$ is 2-thienyl.

30. The compound of claim 28 wherein R$_4$ is 3-thienyl.

31. The compound of claim 28 wherein R$_4$ is phenyl.

32. The compound of claim 28 wherein R$_4$ is 4-hydroxyphenyl.

* * * * *

UNITED STATES PATENT OFFICE
CERTIFICATE OF CORRECTION

Patent No. 4,038,271  Dated July 26, 1977

Inventor(s) Hermann Breuer, Uwe D. Treuner

It is certified that error appears in the above-identified patent and that said Letters Patent are hereby corrected as shown below:

Col. 8, lines 5-9: "e.  6β-[-azabicycloD-[3.2.0](3-Methyl-2,4-dioxo-1-imidazolidinyl)amino-carbonyl]amino]phenylacetyl]-amino]-3,3-dimethyl-7-oxo-4-thia-1-azabicyclo[3.2.0]heptane-2-carboxylic acid, sodium salt"

should read:  -- e.  6β-[[D-[[[3-Methyl-2,4-dioxo-1-imidazolidinyl)amino]-carbonyl]amino]phenylacetyl]amino]-3,3-dimethyl-7-oxo-4-thia-1-azabicyclo[3.2.0]heptane-2-carboxylic acid, sodium salt --.

In Examples 5-36, line 35, "and the 6β-acyl-6βmethoxy" should read:  -- and the 6β-acyl-6α-methoxy --.

In Example 38, line 44, "amino]benzeneacetic" should read: --amino]benzene acetic --.

In Example 38, line 49, "carbonyl]amin0]" should read: -- carbonyl]amino] --.

Signed and Sealed this

Twenty-second Day of November 1977

[SEAL]

Attest:

RUTH C. MASON
*Attesting Officer*

LUTRELLE F. PARKER
*Acting Commissioner of Patents and Trademarks*